United States Patent [19]

Baggio et al.

[11] Patent Number: 4,890,244
[45] Date of Patent: Dec. 26, 1989

[54] DEVICE FOR INSPECTING THE HEAT INSULATION OF HOUSEHOLD APPLIANCES, MORE PARTICULARLY REFRIGERATORS

[75] Inventors: Dino Baggio, Pordenone; Antonio Boscolo, Trieste, both of Italy

[73] Assignee: Zeltron - Instituto Zanussi per la Ricerca S.p.A., Udine, Italy

[21] Appl. No.: 72,844

[22] Filed: Jul. 9, 1987

[30] Foreign Application Priority Data

Jul. 9, 1986 [IT] Italy .............................. 45735 A/86

[51] Int. Cl.$^4$ ......................... G01K 1/16; G06F 15/20
[52] U.S. Cl. ............................... 364/551.01; 364/557; 356/51; 374/137
[58] Field of Search ................. 364/551, 557; 374/137, 374/121, 124, 4, 162; 356/43, 51; 250/342, 330, 334

[56] References Cited

U.S. PATENT DOCUMENTS

| | | | |
|---|---|---|---|
| 3,596,519 | 8/1971 | Blonder et al. | 374/124 |
| 4,343,182 | 8/1982 | Pompei | 374/124 |
| 4,440,509 | 4/1984 | Agarawl | 374/137 |
| 4,733,175 | 3/1988 | Levinson | 374/137 |
| 4,737,917 | 4/1988 | Perron | 374/137 |

Primary Examiner—Parshotam S. Lall
Assistant Examiner—Ellis B. Ramirez
Attorney, Agent, or Firm—Wenderoth, Lind & Ponack

[57] ABSTRACT

A device for inspecting the heat insulation of household appliances, more particularly refrigerators, includes a traditional thermographic apparatus for detecting the thermographic images of the insulation by use of the exothermic reaction produced during foaming of the insulation and a control and processing unit, known per se, connected to the thermographic apparatus, possibly to a monitor, and to an input unit. The control and processing unit contains coded data corresponding to the conditions under which the heat insulation is properly produced, such data being compared with that produced by the thermographic apparatus and corresponding to the effective condition of the heat insulation of each applicance produced. Depending on this comparison, the unit proceeds to control the forward movement of a conveyor device so as to enable the appliances to be assembled, repaired or replaced.

32 Claims, 1 Drawing Sheet

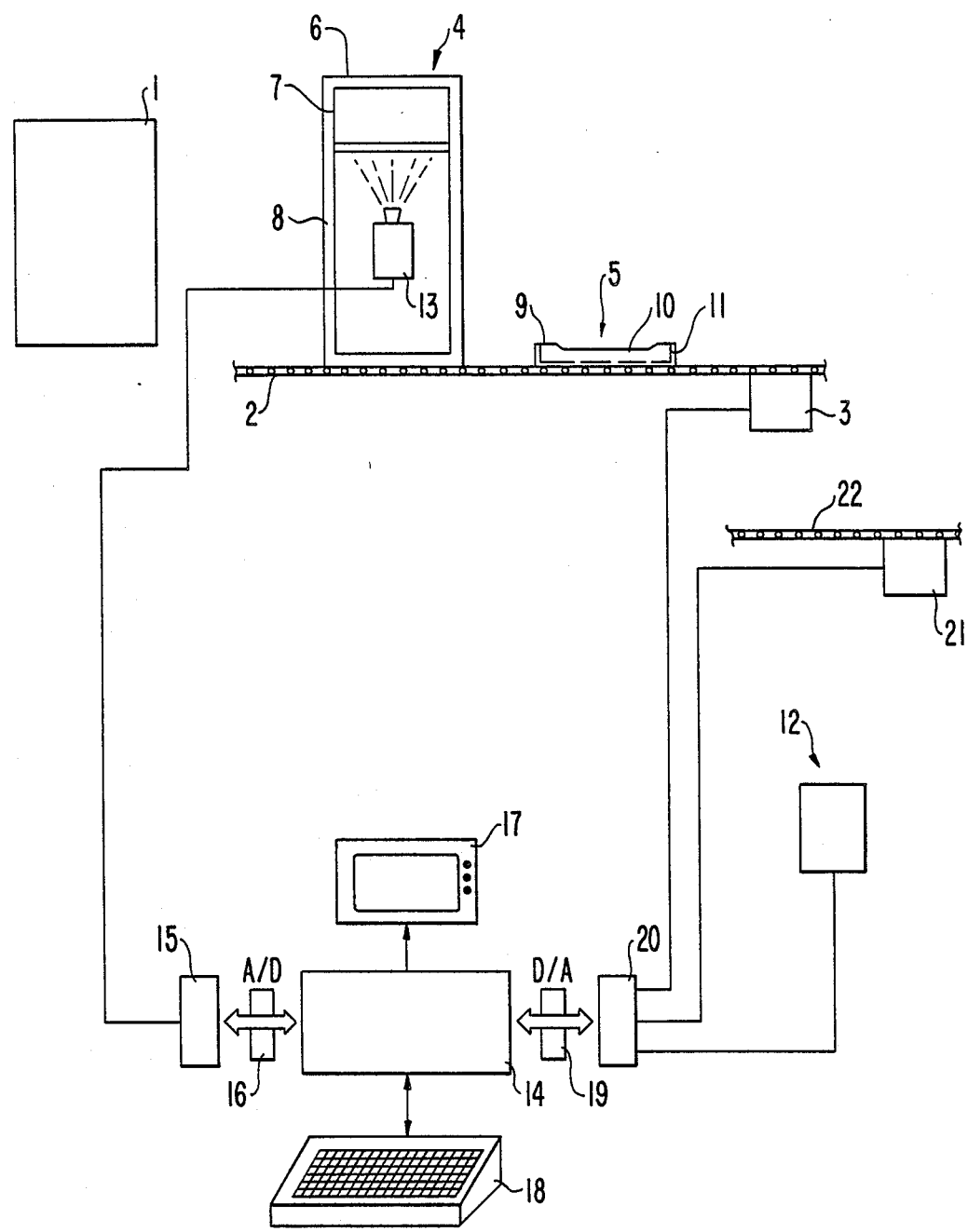

DEVICE FOR INSPECTING THE HEAT INSULATION OF HOUSEHOLD APPLIANCES, MORE PARTICULARLY REFRIGERATORS

BACKGROUND OF THE INVENTION

The invention relates to a device for inspecting the heat insulation of household appliances, more particularly refrigerators, such device being capable of detecting immediately and in a simple manner any deficiencies in the heat insulation during the manufacture of the appliances.

Nowadays, the mass production of a household appliance such as a refrigerator comprises the prefabrication of the body thereof in the form of a metal cabinet which is of substantially parallelepipedal shape and is open on its front side, and of a plastic cell of traditional type dimensioned to fit within such cabinet so as to define therewith an intervening space adapted to receive heat insulation.

The body, in turn, is provided with suitable fixtures for the attachment of a closure door on the front side of the cabinet, such door likewise being of parallelepipedal shape and comprising an outer metal covering and an inner door of plastic material, which elements can be fitted together so as to define an intermediate space adapted to receive heat insulation.

In practice, each door of the refrigerator is made separately from the corresponding body and each of these components is then transported separately by means known per se on a conveyor belt of an assembly line for carrying out processing steps adapted to produce, one after the other, the heat insulation of the body and of the door, as well as the assembling of the body with the door and with other operating components of the refrigerator.

In particular, this heat insulation is obtained by means of polyurethane materials which are known per se, and the liquid components of which are injected separately by traditional apparatus provided along the conveyor belt involved within the corresponding intermediate spaces in the body and the door, in which spaces such components polymerize (so-called foaming operation) and spread out in such a manner as to occupy all of such intermediate spaces.

In order to be able to carry out the foaming operations of the refrigerators satisfactorily, without defects being present in the heat insulation of such appliances, it is necessary that the equipment involved be caused to operate under the same operating and environmental conditions throughout the foaming operation and, furthermore, that the areas of injection of the bodies and doors of the respective refrigerators permit the effective penetration of the polyurethane material into the respective intermediate spaces of the bodies and doors.

In practice, however, such equipment is subject to operating and environmental conditions which at times vary during the foaming of the appliances in question, while the areas of injection of the polyurethane material themselves can, at times, have structural defects such as partly to prevent the penetration and proper distribution of the material throughout the above-described spaces.

Accordingly, under such conditions, defects may appear in the heat insulation of the refrigerators, due primarily to the presence of areas which are without polyurethane material (continuous and non-continuous holes) and areas in which such material is not completely polymerized (so-called "exhausted foam"), which defects result in a decrease of the insulating power of the layer of material and, in certain cases, even in the formation of heat bridges which significantly impair the functionality of the product.

At the present time, the presence of any defects of this type in the heat insulation of refrigerators is detected by the workers during the manufacture of these appliances by means of a number of visual and manual inspections in the areas of the appliances themselves in which such defects are most likely to be located.

While, on the one hand, this type of inspection makes it possible to single out practically all appliances that have defects located in areas which are directly noticeable from the outside, so that it is possible to discard such defective appliances or to perform operations thereon aimed at eliminating the defects found, this method is not, on the other hand, completely reliable in that it does not enable one to accurately examine the entire structure of the heat insulation and thus to single out any defective areas which are found in the insulation itself or which are difficult to locate by the inspections indicated above.

SUMMARY OF THE INVENTION

Therefore, it would be desirable, and this is the object of the present invention, to provide for a device for inspecting the heat insulation or insulation characteristics of household appliances such as refrigerators, which device can immediately and automatically detect the possible presence of defects of any kind and size in the insulation during the production stages of these appliances, thereby obtaining a thorough check of all the appliances manufactured and making it possible to eliminate, or possibly repair, defective appliances.

This inspection device is essentially based on the use of at least one traditional thermographic apparatus for detecting the images produced by the heat insulation of the refrigerators as well as comparing the coded data obtained by such apparatus with other coded data corresponding to optimal functional conditions of the heat insulation, so that from such comparison the presence of any defects of the insulation can be detected immediately.

This technique of detecting thermographic images is used at present in combination with any preexisting type of heat insulation and provides for the detection by the thermographic apparatus of heat radiation passing through the insulation and produced by a suitable separate heat source.

The thermographic images thus produced are visible on the screen of a monitor associated with the apparatus and produce colors of different intensity, depending on the defective areas and on the areas with different densities of the heat insulation.

The present inspection system, however, makes it possible to point out the heat images of the insulation by utilizing the thermal radiation produced by the insulation during its foaming as a result of the corresponding chemical reaction, rather than that produced by a separate heat source as in the past.

These and other objects are achieved, in accordance with the invention, by means of a device for inspecting the heat insulation of household appliances, more particularly refrigerators, which can be used in combination with a plant for the manufacture of such appliances and including means for the foaming of the heat insulation of the appliances by use of polyurethane or similar materials as well as means for the transportation of the appliances. The device includes at least one thermographic apparatus associated with any monitor of traditional type in order to detect the thermographic images of the insulation.

The inspection device also includes at least one control and processing unit known per se containing a series of coded reference data corresponding to the correct production of the heat insulation of each type of household appliance to be produced. The control and processing unit is connected to the thermographic apparatus, to the conveyor means and to at least one input unit known per se for selecting the coded reference data corresponding to the model of household appliance which is to be produced in order to input such coded data into the control and processing unit with the object of comparing it with the coded data supplied by the thermographic apparatus and corresponding to the thermographic images detected thereby, in the presence of the exothermic reaction of the material of the heat insulation during its foaming. The control and processing unit supplies, as a result of such comparison, coded response data adapted to control the conveyor means.

BRIEF DESCRIPTION OF THE DRAWING

Other aspects of the invention will become more apparent from the ensuing description given solely by way of non-limiting example, reference being had to the accompanying drawing which diagrammatically shows the inspection device of the invention used in combination with a traditional manufacturing plant for household refrigerators.

DETAILED DESCRIPTION OF THE INVENTION

Now, with reference to the drawing, it shows the present device for inspecting the heat insulation of household appliances, in the present example refrigerators, which can be assembled in a manufacturing plant comprising at least one traditional apparatus 1 for the foaming of heat insulation by means of polyurethane or similar materials, and also comprising a transport means such as a conveyor belt 2 of known construction. Conveyor belt 2, in particular, can be driven with a continuous forward motion by drive mechanisms known per se denoted diagrammatically by the reference numeral 3, so as to permit the transportation and assembly of the various elements constituting each refrigerator, that is to say, the body 4 and the door 5.

Each body 4 is formed, as in the prior art, of a metal cabinet 6 which is of a substantially parallelepipedal shape and has dimensions which may vary from one appliance model to the next, cabinet 6 being open on its front side and being adapted to contain a plastic cell 7 of traditional type dimensioned such as to fit perfectly within cabinet 6, in order to define therewith an intermediate space 8 in which the heat insulation is foamed.

Each door 5, in turn, is also of parallelepipedal shape and is formed of an outer metal covering 9 and an inner door 10 of plastic, the shapes of both being adapted to each other so as to define an intermediate space 11 into which the heat insulation is foamed.

As an alternative, the transportion and assembly of the constituent parts of each refrigerator could also be effected by at least one fully automated production line, comprising any possible manipulators 12 or similar apparatus of known construction.

The inspection device incorporating the invention is essentially comprised of at least one traditional thermographic apparatus 13, such as a pyroelectric television camera, a pyrometer or similar sensor adapted to detect heat images of the heat insulation so as directly to evaluate the condition thereof, utilizing the exothermic reaction of the material of such insulation during its foaming.

Preferably, the spectral sensitivity of the television camera or of the sensor in question will be within the region of infrared radiation, with wavelengths equal to those of transparency of the plastic materials used for the construction of the refrigerator bodies and doors, in order to be able to obtain heat images with good definition of the insulation. Such thermographic apparatus, in particular, is connected to an electric power supply and is arranged alongside the heat insulation of the refrigerators located on the conveyor belt 2.

Furthermore, such apparatus can be oriented in different positions with respect to the body and door of each refrigerator so as to be able selectively and accurately to check all those areas of the heat insulation of these constituent parts which have the greatest probability of being defective during manufacture.

As will be apparent from the drawing, the apparatus in question detects the heat images by being aimed exclusively at the respective parts of the body and door of plastic or other material with medium or low heat conductivity in which there is the minimum distribution of heat on the surface as compared with what takes place in the case of metal surfaces.

In addition, the present inspection device comprises at least one control and processing unit 14 made up of a microcomputer, a personal computer or some other processing apparatus of known construction, such unit being connected to the thermographic apparatus 13 by at least one interface 15 and an analog/digital converter 16 of known construction.

In the control and processing unit 14 there has been previously stored data coded in digital form corresponding to reference thermal maps of the heat insulation of each model of refrigerator which is to be manufactured.

In particular, each thermal map is obtained experimentally on a series of models of refrigerators and corresponds to a condition under which the heat insulation of such appliances is produced properly, without the presence of defective areas and under pre-established operating and environmental conditions.

Moreover, control and processing unit 14 is possibly connected to at least one monitor 17 of traditional type for the visual display of the thermographic images of the heat insulation detected by the thermographic apparatus described earlier, and it is also connected to at least one input unit 18 made up of a keyboard or other peripheral equipment of known construction (e.g., bar code readers).

The purpose of the input unit 18 is to select coded data corresponding to the reference thermal map relative to the model of refrigerator (or other household appliance) which is to be produced, in order to input such coded data into the control and processing unit 14 so that said such reference thermal map can be compared therein with the thermal map found on each refrigerator manufactured by the procedure described hereinafter.

Furthermore, the input unit 18 makes possible the introduction of further reference thermal maps in coded form into the control and processing unit 14, whenever other models of refrigerators (or other household appliances) are produced.

In this way, as soon as the thermographic apparatus 13 finds or determines a thermographic image of the area to be checked of the heat insulation of the refrigerator body or door during the course of production thereof, which image is visible to the operator on the monitor 17, if provided, thermographic apparatus 13 produces data coded in analog form which corresponds to such image and which is converted into digital form by the analog/digital converter 16 and sent to the control and processing unit 14. This coded data is then compared in the unit 14 with the coded data corresponding to the relevant reference thermal map previously stored in unit 14 in order thereby to be able to verify whether the heat insulation in question has been produced properly and is without manufacturing defects that could reduce its insulating power.

In practice, if such comparison shows minimum differences between the corresponding coded data of the heat image found or determined and the reference map in question, which differences are, however, within a preestablished range of tolerance corresponding to the proper production of the heat insulation, then the control and processing unit 14 proceeds to process corresponding coded response data in digital form, which may be converted into analog form by a digital/analog converter 19 and sent to an interface 20 adapted to control the drive mechanisms 3 and thereby to cause the conveyor belt 2 to move forward.

Accordingly, under these circumstances, the assembling of the refrigerator which has thus been inspected can be completed.

Conversely, if the comparison between such coded data shows differences that do not fall within the specified range of tolerance, the control and processing unit 14 proceeds to process corresponding response data which are adapted to control, by the same procedures described earlier, another drive mechanism 21 which is associated with an auxiliary conveyor belt 22 so as to enable repair work to be performed on the defects found, for instance further foaming of the heat insulation or, if this is not possible, transporting the defective appliances for scrapping or replacement.

Similarly, if the refrigerator manufacturing plant consists of mechanical manipulators 12 or other apparatus for automatic assembly instead of conveyor belts, the control and processing unit 14 proceeds to control such manipulators under the same criteria and for the same purposes as described above. Therefore, the inspection device of the invention makes it possible to find in a simple, immediate and automatic manner any defect in the heat insulation of the appliances produced, thereby achieving a complete inspection of all the appliances and the maximum degree of reliability of the plant for their manufacture, and furthermore permitting the elimination or repair of defective appliances.

The present inspection device can, of course, also be combined with plants for the manufacture of products other than those described herein, for instance for producing slabs of acoustic or thermal insulating materials, etc., their essential characteristics being that they develop an exothermic reaction during manufacture.

Finally, it should be pointed out that the inspection device of the invention can also be provided with further thermographic apparatus 13 which can be switched selectively with the control and processing unit 14 by means known per se (e.g., a multiplexer or the like) and arranged along different areas of the heat insulation of one or more appliances during the course of manufacture thereof.

I claim:

1. In a plant for manufacturing a product including insulation material, said plant including means for forming the insulation material by foaming a polyurethane or similar material, thereby causing an exothermic reaction, and transport means for moving the product through said plant during the manufacture thereof, the improvement comprising means for inspecting the insulation characteristics of the insulation material, said inspecting means comprising:

thermographic means to be directed toward the product for, during said foaming, detecting a heat image of said insulation material as a function of said exothermic reaction and for generating detected coded data representative thereof;

processing and control means containing reference coded data representative of a heat image of insulation material of acceptable insulation characteristics and operatively connected to said thermographic means for receiving said detected coded data therefrom, for comparing said detected coded data with said reference coded data, and for generating coded response data as a function of such comparison; and said processing and control means being operatively connected to said transport means for controlling the operation of said transport means as a function of said coded response data.

2. The improvement claimed in claim 1, wherein said processing and control means contains plural reference coded data representative of heat images of insulation material of acceptable insulation characteristics of respective different products, and further comprising input means operatively connected to said processing and control means for selecting a respective said reference coded data corresponding to a particular product to be manufactured.

3. The improvement claimed in claim 1, further comprising a monitor connected to said processing and control means for visually displaying said detected heat image.

4. The improvement claimed in claim 1, wherein said thermographic means is capable of orientation toward plural different areas of the product.

5. The improvement claimed in claim 1, wherein said transport means comprises a conveyor for moving products through said plant, and further comprising an auxiliary conveyor for conveying defective products, said processing and control means causing said conveyor or said auxiliary conveyor to operate as a function of said coded response data being respectively within or without a predetermined range.

6. The improvement claimed in claim 1, further comprising at least one additional thermographic means, and means for selectively switching said thermographic means and said at least one additional thermographic means into and out of operative connection with said processing and control means.

7. The improvement claimed in claim 1, wherein said thermographic means is connected to said processing and control means by an interface.

8. The improvement claimed in claim 7, wherein said thermographic means further is connected to said processing and control means by an analog/digital converter.

9. The improvement claimed in claim 1, wherein said processing and control means is connected to said transport means by an interface.

10. The improvement claimed in claim 9, wherein said processing and control means further is connected to said transport means by a digital/analog converter.

11. An inspecting device, for use in a plant for manufacturing a product including insulation material, said plant including means for forming the insulation material by forming a polyurethane or similar material, thereby causing an exothermic reaction, and transport means for moving the product through the plant during the manufacture thereof, means for inspecting the insulation characteristics of the insulation material, said inspecting means comprising:

thermographic means to be directed toward the product for, during the foaming operation, detecting a heat image of the insulation material as a function of said exothermic reaction and for generating detected coded data representative thereof;

processing and control means containing reference coded data representative of a heat image of insulation material of acceptable insulation characteristics and operatively connected to said thermographic means for receiving said detected coded data therefrom, for comparing said detected coded data with said reference coded data, and for generating coded response data as a function of such comparison; and said processing and control means including means to be operatively connected to the transport means for controlling the operation of the transport means as a function of said coded response data.

12. A device as claimed in claim 11, wherein said processing and control means contains plural reference coded data representative of heat images of insulation material of acceptable insulation characteristics of respective different products, and further comprising input means operatively connected to said processing and control means for selecting a respective said reference coded data corresponding to a particular product to be manufactured.

13. A device as claimed in claim 11, further comprising a monitor connected to said processing and control means for visually displaying said detected heat image.

14. A device as claimed in claim 11, wherein said thermographic means is capable of orientation toward plural different areas of the product.

15. A device as claimed in claim 11, wherein said thermographic means is connected to said processing and control means by an interface.

16. A device as claimed in claim 15, wherein said thermographic means further is connected to said processing and control means by an analog/digital converter.

17. A device as claimed in claim 11, further comprising an interface for connecting said processing and control means to the transport means.

18. A device as claimed in claim 17, further comprising a digital/analog converter for further connecting said processing and control means to the transport means.

19. A device as claimed in claim 11, wherein the transport means comprises a conveyor for moving products through said plant and auxiliary conveyor for conveying defective products, and said processing and control means causes the conveyor or the auxiliary conveyor to operate as a function of said coded response data being respectively within or without a predetermined range.

20. A device as claimed in claim 11, further comprising at least one additional thermographic means, and means for selectively switching said thermographic means and said at least one additional thermographic means into and out of operative connection with said processing and control means.

21. In a process for manufacturing a product including insulation material, said process including forming the insulation material by foaming a polyurethane or similar material, thereby causing an exothermic reaction, and moving said product by transport means during the manufacture thereof, the improvement comprising inspecting the insulation characteristics of said insulation material, said inspecting comprising:

directing thermographic means toward said product and thereby, during said foaming, detecting a heat image of said insulation material as a function of said exothermic reaction and for generating detected coded data representative thereof;

providing processing and control means containing reference coded data representative of a heat image of insulation material of acceptable insulation characteristics;

delivering said detected coded data from said thermographic means to said processing and control means and therein comparing said detected coded data with said reference coded data and generating coded response data as a function of such comparison; and controlling the operation of said transport means as a function of said coded response data.

22. The improvement claimed in claim 21, comprising provided said processing and control means with plural reference coded data representative of heat images of insulation material of acceptable insulation characteristics of respective different products, and inputting to said processing and control means a selected respective said reference coded data corresponding to a particular product to be manufactured.

23. The improvement claimed in claim 21, further comprising visually displaying said detected heat image on a monitor connected to said processing and control means.

24. The improvement claimed in claim 21, further comprising orienting said thermographic means toward plural different areas of said product.

25. The improvement claimed in claim 21, wherein said transport means comprises a conveyor for moving products and an auxiliary conveyor for conveying defective products, and further comprising causing said processing and control means to operate said conveyor or said auxiliary conveyor as a function of said coded response data being respectively within or without a predetermined range.

26. The improvement claimed in claim 21, further comprising providing at least one additional thermographic means, and selectively switching said thermographic means and said at least one additional thermographic means into and out of operative connection with said processing and control means.

27. The improvement claimed in claim 21, comprising connecting said thermographic means to said processing and control means by an interface.

28. The improvement claimed in claim 27, further comprising connecting said thermographic means to said processing and control means by an analog/digital converter.

29. The improvement claimed in claim 21, comprising connecting said processing and control means to said transport means by an interface.

30. The improvement claimed in claim 29, further comprising connecting said processing and control means to said transport means by a digital/analog converter.

31. The improvement claimed in claim 21, wherein said product is a household appliance and said insulation material is thermal insulation.

32. The improvement claimed in claim 31, wherein said product is a refrigerator.

* * * * *

UNITED STATES PATENT AND TRADEMARK OFFICE
CERTIFICATE OF CORRECTION

PATENT NO. : 4,890,244

DATED : December 26, 1989

INVENTOR(S) : Dino BAGGIO and Antonio BOSCOLO

It is certified that error appears in the above-identified patent and that said Letters Patent is hereby corrected as shown below:

On the Cover Page, change "Assignee: Zeltron - Instituto Zanussi per la Ricerca S.p.A., Udine, Italy" to --Assignee: Industrie Zanussi S.p.A., Pordenone, Italy--.

Signed and Sealed this

Thirteenth Day of August, 1991

*Attest:*

HARRY F. MANBECK, JR.

*Attesting Officer*  *Commissioner of Patents and Trademarks*